United States Patent
Fisk

(10) Patent No.: US 8,948,881 B2
(45) Date of Patent: Feb. 3, 2015

(54) METHOD FOR PRODUCING IMPLANTABLE ELECTRODE COATINGS WITH A PLURALITY OF MORPHOLOGIES

(75) Inventor: Andrew E. Fisk, Philadelphia, PA (US)

(73) Assignee: Greatbatch Ltd., Clarence, NY (US)

(*) Notice: Subject to any disclaimer, the term of this patent is extended or adjusted under 35 U.S.C. 154(b) by 1135 days.

(21) Appl. No.: 11/750,597

(22) Filed: May 18, 2007

(65) Prior Publication Data

US 2007/0270927 A1    Nov. 22, 2007

Related U.S. Application Data

(60) Provisional application No. 60/747,672, filed on May 19, 2006.

(51) Int. Cl.
*A61N 1/05* (2006.01)

(52) U.S. Cl.
CPC ............... *A61N 1/05* (2013.01); *A61N 1/0565* (2013.01)
USPC .......................................... 607/119; 607/116

(58) Field of Classification Search
USPC ..................... 607/9, 116, 119–121, 125–131; 600/373–377, 395; 977/701, 707, 722, 977/773, 777, 811, 904, 920, 931; 429/137, 429/209–231.95
See application file for complete search history.

(56) References Cited

U.S. PATENT DOCUMENTS

| | | | |
|---|---|---|---|
| 4,602,637 A | | 7/1986 | Elmqvist et al. |
| 4,611,604 A | | 9/1986 | Botvidsson et al. |
| 4,663,256 A | | 5/1987 | Corrigan |
| 5,318,572 A | * | 6/1994 | Helland et al. ............... 607/121 |
| 5,486,277 A | | 1/1996 | Barbee, Jr. et al. |
| 5,624,769 A | | 4/1997 | Li et al. |
| 6,319,293 B1 | * | 11/2001 | Debe et al. ................... 29/623.3 |
| 6,799,076 B2 | * | 9/2004 | Gelb et al. ................... 607/121 |

(Continued)

FOREIGN PATENT DOCUMENTS

EP    1 454 651 A1    9/2004

OTHER PUBLICATIONS

Growth and Properties of Single Crystal Tin Films Deposited by Reactive Magnetron Sputtering—B.O. Johansson, J.E. Sundgren and J.E. Greene, J. Vac. Sci, Technol. A3(S).

(Continued)

*Primary Examiner* — Kennedy Schaetzle
*Assistant Examiner* — Erica Lee
(74) *Attorney, Agent, or Firm* — Michael F. Scalise

(57) ABSTRACT

An implantable electrode comprising a substrate supporting microscopic surface structures such as columnar titanium nitride and further having nanoscopic surface structures on titanium nitride deposited on the exposed surface of the microscopic columnar structures is described. This is done through physical vapor deposition (PVD) and is based upon a relatively abrupt change in the surface mobility of the depositing material with a consequential variation in nucleation site density and surface mobility. At low mobility, there are increased nucleation sites and the condensation features are more numerous and finer. As mobility of the deposited species increases, the nucleation sites in the condensate film become fewer with coarser features. Consequently, the change from a relatively coarse microscopic surface structure to a relatively fine nanoscopic surface structure is accomplished by abruptly changing the total gas pressure in the processing chamber within a relatively short period of time of about ten seconds, or less.

26 Claims, 10 Drawing Sheets

(56) References Cited

U.S. PATENT DOCUMENTS

| | | |
|---|---|---|
| 6,805,998 B2 | 10/2004 | Jenson et al. |
| 6,960,378 B1 * | 11/2005 | Siegel et al. ............... 428/36.9 |
| 6,962,613 B2 | 11/2005 | Jenson |
| 7,052,802 B2 | 5/2006 | Tsukamoto et al. |
| 7,079,903 B2 | 7/2006 | O'Brien |
| 7,194,315 B1 | 3/2007 | Platt et al. |
| 2001/0032005 A1 | 10/2001 | Gelb et al. |
| 2003/0165731 A1 | 9/2003 | Vyas et al. |
| 2004/0048157 A1 | 3/2004 | Neudecker et al. |
| 2004/0220652 A1 | 11/2004 | Zhou et al. |
| 2004/0240155 A1 | 12/2004 | Miltich et al. |
| 2004/0242953 A1 * | 12/2004 | Good ............................ 600/7 |
| 2005/0203604 A1 * | 9/2005 | Brabec et al. ............... 607/122 |
| 2005/0235869 A1 * | 10/2005 | Cruchon-Dupeyrat et al. ............... 106/31.29 |
| 2005/0247379 A1 * | 11/2005 | Klein et al. ............... 148/430 |
| 2006/0015026 A1 | 1/2006 | Glocker et al. |
| 2006/0019157 A1 | 1/2006 | Jenson |
| 2006/0162150 A1 | 7/2006 | Tsukamoto et al. |
| 2006/0193889 A1 * | 8/2006 | Spradlin et al. ............... 424/423 |

OTHER PUBLICATIONS

Bolz, Armin: "Die Bedetung Der Phasengrenze Zwischen Alloplastischen Festkorpern Und Biologischen Geweben Fur Die Elektrostimulation" 1995, Fachverlag Schiele & Schon, Berlin.

* cited by examiner

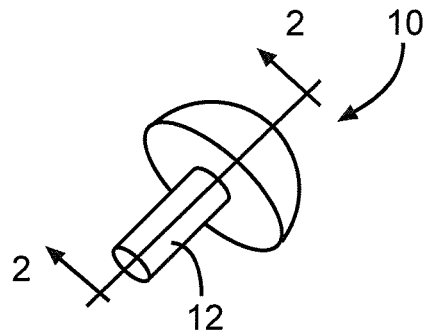
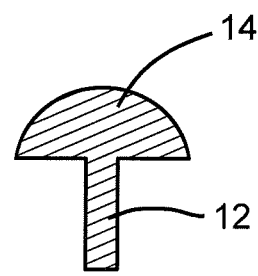
FIG. 1
Prior Art
FIG. 2
Prior Art
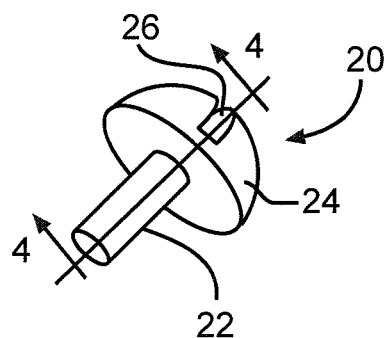
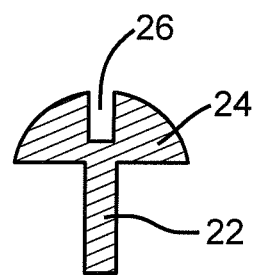
FIG. 3
Prior Art
FIG. 4
Prior Art
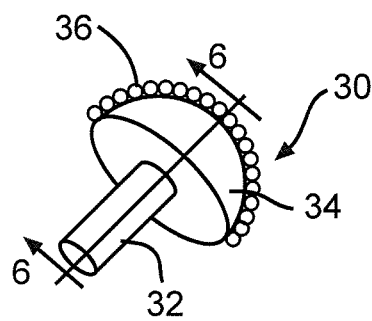
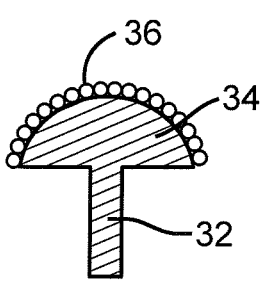
FIG. 5
Prior Art
FIG. 6
Prior Art

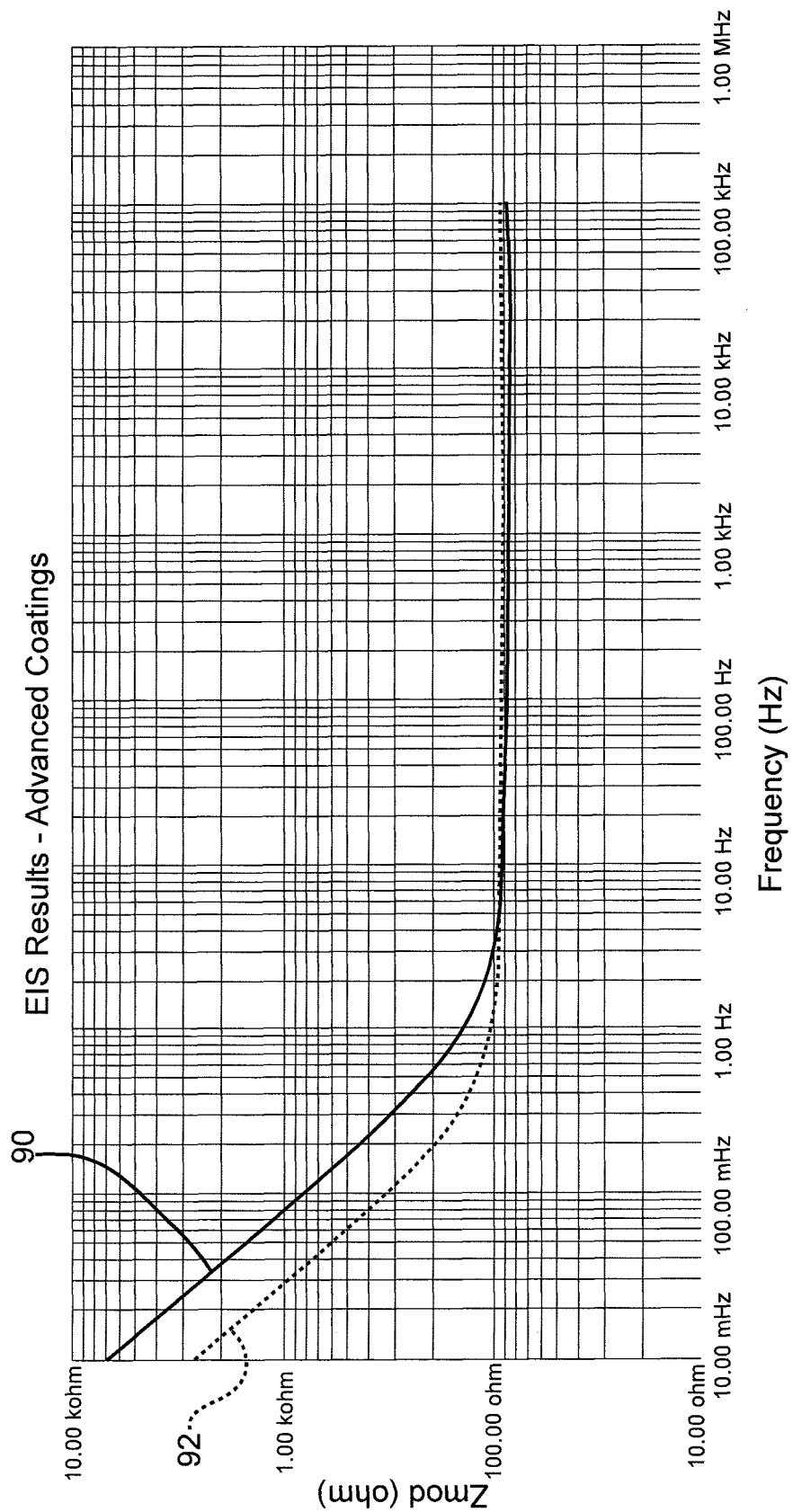

METHOD FOR PRODUCING IMPLANTABLE ELECTRODE COATINGS WITH A PLURALITY OF MORPHOLOGIES

CROSS-REFERENCE TO RELATED APPLICATION

This application claims priority from U.S. Provisional Application Ser. No. 60/747,672, filed May 19, 2006.

BACKGROUND OF THE INVENTION

1. Field of the Invention

This invention relates to coatings for implantable electrodes such as pacing electrodes, neurostimulator electrodes, electroporating electrodes, and sensing electrodes. More particularly, the present invention is directed to the creation of additional porosity and thereby additional surface area in an implantable electrode.

The three overriding requirements for implantable electrodes are biocompatibility, biostability, and low energy loss during tissue stimulation. Broadly, the biocompatibility requirement is met if contact of the electrode with body tissue and blood results in little or no immune response from the body, especially thrombogenicity (clotting), infection, and encapsulation of the electrode with fibrotic tissue. The biostability requirement means that all physical, electrical, and chemical properties of the electrode/coating system remain constant and unchanged over the life of the patient. The low energy loss requirement is met if electrode polarization is optimized.

2. Prior Art

U.S. Pat. No. 4,602,637 to Elmqvist et al. teaches that upon stimulation of body tissue the polarization rise of an active surface layer is maintained "very slight" by use of a high double layer capacitance at the phase boundary between the electrode/body fluid. The high double layer capacitance maintains the polarization rise during stimulation pulses (0.5 through 1 ms, 1 Hz, 10 mA, 10 mm$^2$) to less than 0.1 V. This is accomplished through high specific surface area coatings, such as of titanium nitride (TiN), by specifying processing parameters. These parameters utilize low adatom surface mobility and an increase in liberated species collisions to produce pronounced columnar structures of the TiN via physical shadowing. Due to the low surface mobility, discrete nucleation sites are formed on the substrate. During subsequent vapor flux arrival, the already existing deposits physically shadow the un-reacted substrate. Physical shadowing by the major constituent leads to columns.

Other prior art processes for producing electrode coatings exhibiting low polarization rises during stimulation pulses are accomplished by increasing the specific surface area at the phase boundary between the electrode/body fluid. This involves removal of material from an already coated electrode surface. The coating (or bare substrate if no coating is used) is subjected to etching via electrochemical or chemical, ionic or physical means. In the case of electrochemical and chemical etching, an agent that leaves holes by preferentially attacking the major constituent is used. The difference between electrochemical and chemical etching is that the former includes an electrolytic bath in which an electrical bias helps with the etching process and the latter does not.

In the case of ionic cleaning or etching, the surface of the coating is bombarded with ions, thus preferentially etching the areas of low radius. This ionic etching can also incorporate a screen for imparting patterns on the surface. In the case of physical etching, mechanical means are used to remove surface layers and increase surface area. This is done by employing techniques such as laser machining and grit blasting.

For a better understanding of electrodes having features imparting high specific surface area, reference is made to the drawings. Throughout this disclosure, the term "specific surface" refers to the ratio between all surface areas that are capable of undergoing electrochemical activity while in service and the geometric surface area of the exposed part of the electrode body. This includes surface roughness, porosity, and convolution.

The porosity of a coating consists of three types of porosity features, macroscopic, microscopic and nanoscopic. A macroscopic surface has details characterized by features ranging from about 10 µm to about 1,000 µm. Microscopic features range from about 100 nm to about 1000 nm while nanostructures have features of less than about 50 nm.

FIGS. 1 and 2 show a conventional electrode 10 comprising a shaft 12 joined to a substrate in the form of a head 14 as a unitary member. The electrode 10 is of a material selected from tantalum, titanium, zirconium, iridium, platinum, palladium, niobium, and mixtures thereof. Preferably, the electrode is of platinum/10% iridium. Although the shaft 12 is cylindrical, that is not necessary. Also, the electrode head 14 is shown as a dome-shaped member of a constantly curved radius, but that is also not necessary. That the electrode has a head 14 providing a surface, coated or otherwise, that is capable of a low energy loss transmission of electrical energy into a body tissue is what is relevant.

FIGS. 3 and 4 illustrate a similar conventional electrode 20, but one that has been subjected to mechanical treatment. This electrode 20 comprises a shaft 22 joined to a substrate in the form of a dome-shaped head 24 as a unitary member. However, the head 24 has been provided with a grooved cut-out 26 that is generally centered along the longitudinal axis of the shaft 22. That the groove 26 is centered with the shaft or that there is only one groove is not limiting. The point is that mechanical means such as machine cutting, laser cutting, etching, grit blasting, and the like have been used to increase the active surface area of the head 24 in comparison to the electrode 10 shown in FIGS. 1 and 2.

FIGS. 5 and 6 illustrate an electrode 30 comprising a shaft 32 extending to a head 34 as a unitary member. In that respect, it is similar to the electrode 10 of FIGS. 1 and 2. However, the head 34 has been provided with macroscopic surface structures 36 by the addition of particles ranging in size from about 10 µm to about 1,000 µm. The macroscopic surface structures 36 can be any material that has high biocompatibility, biostability, and electrical conductivity. Examples include carbon, boron, platinum, palladium, iridium, gold, titanium, tantalum, niobium, ruthenium, zirconium, and alloys thereof. In addition, the carbides, nitrides, carbonitrides, and oxides or doped oxides of these metals, and their alloys, may be used including iridium oxide, iridium nitride, titanium nitride, titanium carbide, titanium carbonitride, tantalum nitride, tantalum carbide, tantalum carbonitride, niobium carbide, niobium nitride, niobium carbonitride, ruthenium oxide, ruthenium nitride, zirconium oxide, zirconium nitride, zirconium carbide, and mixtures thereof. In cases where the compounds of the macroscopic surface materials 36 are not electrically conductive, they can be made so by doping with small amounts of extraneous elements. For example, titanium dioxide, a dielectric in its pure state, is made conductive by doping with niobium. Titanium nitride is a particularly preferred material for the macroscopic surface structures 36.

All of these macroscopic surface materials 36 can be applied to the electrode head 34 in such a way that the resulting coatings have high surface areas with very fine scale roughness and porosity. Suitable deposition methods include physical vapor deposition processes such as sputtering (deposition by plasma activation), evaporation (deposition by thermally activated vaporization), pyrolytic deposition (thin film thermally deposited by decomposing a liquid precursor), or by chemical vapor deposition (thin film thermally deposited by decomposing a gaseous precursor).

The electrode 20 of FIGS. 3 and 4 exhibits improved polarization upon stimulation in comparison to the electrode 10 of FIGS. 1 and 2, primarily due to its mechanical structures, i.e. the groove 26. Further, the electrode 30 of FIGS. 5 and 6 exhibits improved polarization in comparison to electrode 20. This is due to the macroscopic surface materials 36 supported on the head 34.

It has been shown that by increasing the specific surface area of a coating, for example a coating of titanium nitride (TiN), the polarization of an electrode can be reduced. Referring again to the drawings, FIG. 7 shows a conventional electrode 40, similar to electrode 30 of FIGS. 5 and 6, comprising a shaft 42 extending to a head 44 provided with microscopic surface structures 46 in the form of columns 48. Exemplary materials for the microscopic surface structures 46 are the same as those of the macroscopic materials 36, with columnar titanium nitride being preferred.

There are two types of porosity that lead to the formation of specific surface area, namely inter-columnar and intra-columnar. As shown in FIG. 8, inter-columnar porosity 50 is formed by voids left between columns 48. This microscopic porosity is seen upon low-resolution investigation, i.e. a magnification of about 2000×. As shown in FIG. 9, intra-columnar porosity 52 is formed within each column 48 by dendrite structures 54 (FIG. 10). This nanoscopic porosity appears as a feathery structure under high-resolution investigation, i.e. a magnification of about 30,000×. It is therefore conceivable that the total porosity of a conventional coating system may be predominately governed by intra-columnar nanoscopic porosity 52 formed in the dendrite structures 54. Small increases in this porosity may lead to ten fold increases in specific surface area. The coated electrode illustrated in FIGS. 7 to 10 yields a total surface area of about 1 $mm^2$ to about 20 $mm^2$.

However, there is still a need for an implantable electrode having the requisite biocompatibility and biostability characteristics, such as provided by columnar titanium nitride, but that advances the state of the art through high specific surface characteristics. The result is an electrode with a lower polarization rise upon stimulation than is currently provided by columnar titanium nitride, and the like. The present electrode fulfills this need in terms of both low polarization and minimum energy requirements for acceptable sensing properties by the incorporation of secondary nanoscopic structures supported on the columnar microscopic structures 48.

The foregoing and additional objects, advantages, and characterizing features of the present invention will become increasingly more apparent upon a reading of the following detailed description together with the included drawings.

BRIEF DESCRIPTION OF THE DRAWINGS

FIG. 1 is a perspective view of a conventional electrode 10 comprising a shaft 12 joined to a head 14.
FIG. 2 is a cross-sectional view along line 2-2 of FIG. 1.
FIG. 3 is a perspective view of a conventional electrode 20 comprising a shaft 22 joined to a head 24 provided with a groove 26.
FIG. 4 is a cross-sectional view along line 4-4 of FIG. 3.
FIG. 5 is a perspective view of a conventional electrode 30 comprising a shaft 32 joined to a head 34 supporting columnar structures 36.
FIG. 6 is a cross-sectional view along line 6-6 of FIG. 5.
FIG. 20 is a graph showing the EIS results of an electrode made according to conventional practice in comparison to the same electrode after having undergone further processing to provide secondary nanoscopic surface structures.

DETAILED DESCRIPTION OF THE PREFERRED EMBODIMENTS

According to the present invention the microscopic and nanoscopic porosity of a coating can be further optimized to greatly increase an electrode's specific surface area at the boundary between the electrode/body fluid interphase. For example, it is known that the addition of microscopic porosity, i.e. columnar titanium nitride, can increase the specific surface area of a coating by from about 100 to 400 times.

Figure 7:
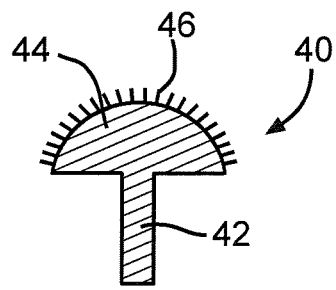
FIG. 7 is a cross-sectional view of a conventional electrode 40 provided with microscopic surface structures 46 supported on its head 44.
Figure 8:
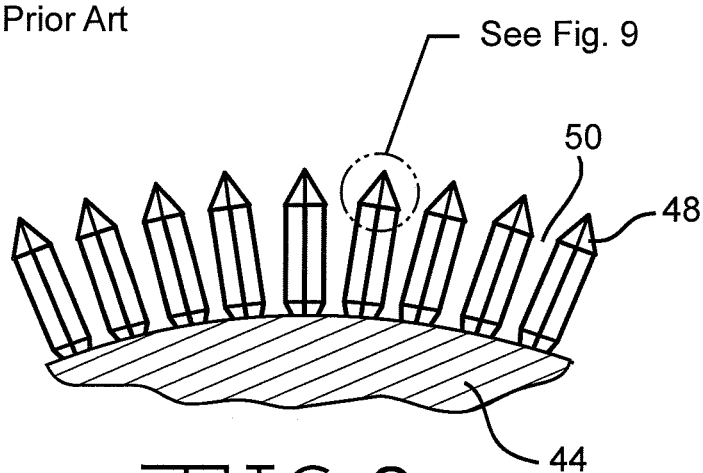
FIG. 8 is an enlarged view of the microscopic surface structures 46 in FIG. 7 in the form of a microscopic column structure 48.
Figure 9:
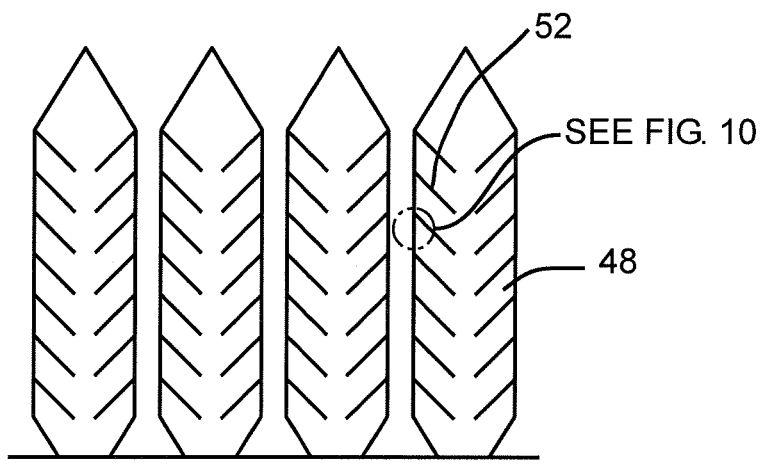
FIG. 9 is an enlarged view of the indicated area in FIG. 8.
Figure 10:
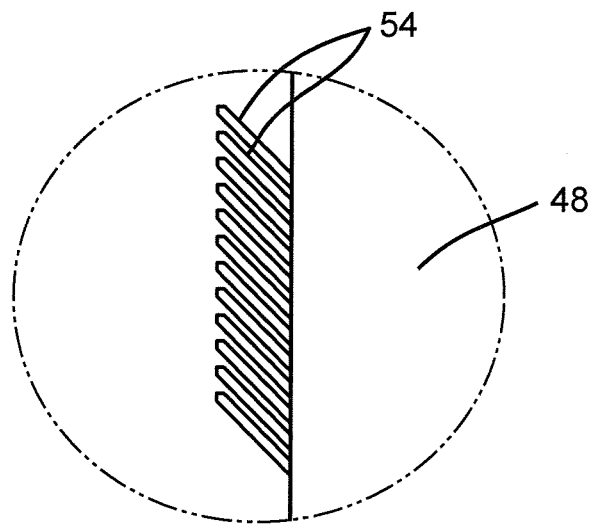
FIG. 10 is an enlarged view of the indicated area in FIG. 9.
Figure 11:
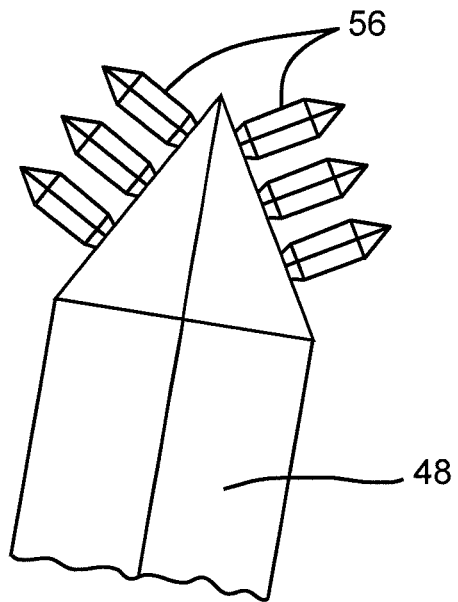
FIG. 11 is a broken-away perspective view of nanoscopic structures 56 supported on a microscopic columnar structure 48 according to the present invention.

FIG. 11 illustrates a coating according to the present invention in which nanoscopic surface structures 56 have been deposited on the exposed surface of the microscopic columnar structures 48. The nanoscopic columnar structures 56 are in addition to the nanoscopic dendritic structures 54. This means that an optimal balance must be struck between microscopic and nanoscopic surface features. This is done through physical vapor deposition (PVD). The PVD process known as magnetron sputtering is preferred. The magnetron sputtering process consists of the removal of material from a cathodic target and its subsequent condensation (deposition) on a substrate. This takes place in a vacuum and may utilize a reactive gas to form nitrides, oxides or carbides of the target material.

The present invention has been demonstrated using TiN as the material for both the microscopic and nanoscopic features. The process of producing the microscopic and nanoscopic features is based upon a relatively abrupt change in the surface mobility of the depositing material with a consequential variation in nucleation site density and surface mobility. At low mobility, there are increased nucleation sites and, consequently, the condensation features are more numerous and finer. As mobility of the deposited species increases, the nucleation sites in the condensate film become fewer with coarser features. It is known that the main factors affecting mobility are substrate temperature and total gas pressure within the vacuum of the PVD chamber. Due to the nature of the PVD process, however, heat is generated during deposition. Consequently, pressure variation is the preferred method for producing an abrupt change in surface features or morphology. According to the present invention, the change from a relatively coarse microscopic surface structure to a relatively fine nanoscopic surface structure is accomplished by abruptly changing the total gas pressure within the processing chamber. So long as the pressure change happens within a relatively short period of time of about ten seconds, or less, this may be done without interrupting the process.

Thus, the preferred embodiment of the invention calls for forming a TiN coating using DC, reactive magnetron sputtering. The cathode power density is from about 1 W/cm$^2$ to about 15 W/cm$^2$, preferably, from about 5 W/cm$^2$ to about 9 W/cm$^2$. The ratio of nitrogen to argon gas flow (N:Ar) in the chamber is from about 100:0 to about 20:80, preferably from about 60:40 to about 30:70. The pressure in the deposition chamber should be from about 1 mTorr to about 75 mTorr.

The microscopic structures 48 are formed with a pressure of from about 3 mTorr to about 12.5 mTorr, preferably from about 3 mTorr to about 10 mTorr. Then, the nanoscopic structures 56 are formed with a pressure of from about 12.5 mTorr to about 35 mTorr, preferably from about 15 mTorr to about 35 mTorr. The change in pressure should occur within about ten seconds to effectively increase the nucleation sites and decrease the feature size of the structures.

It is within the scope of the present invention that the microscopic structures 48 can be deposited and then the deposition process is discontinued for a period of time. The electrode can be removed from the vacuum and stored for further processing at a later time. That is when the nanoscopic structures 56 are deposited. Further, the materials of the microscopic structures 48 and the nanoscopic structures 56 are preferably the same. However, they can be of different materials by depositing the respective structures using different targets in the physical vapor deposition chamber. Storage under inert conditions, for example, in a nitrogen box or in a vacuum sealed pouch, and for a limited timeframe, ideally less than about 24 hours, is preferred. Just prior to re-fixturing and depositing of the nanoscopic structures 56, parts may be cleaned via plasma etching or setting the coating equipment to first reverse sputter and then to the deposition settings. The use of disparate targets to deposit different materials in a PVD process is known by those skilled in the art.

Figure 12:
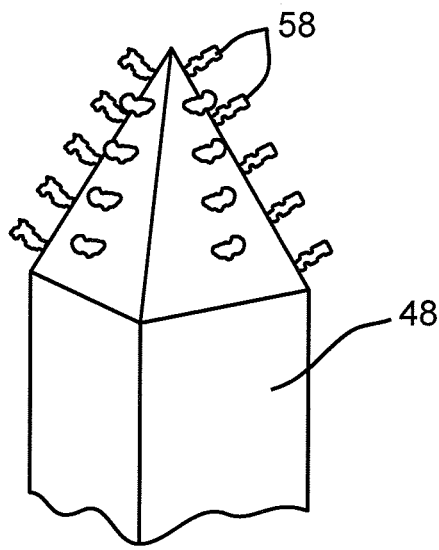
FIG. 12 illustrates one embodiment of the invention where the nanoscopic structures 58 are in the form of plumes of dendrites supported on the microscopic columnar structure 48.

FIG. 12 illustrates one embodiment of the invention where the nanoscopic structures 58 are in the form of plumes of dendrites supported on the microscopic columnar structures 48, such as of titanium nitride.

Figure 13:
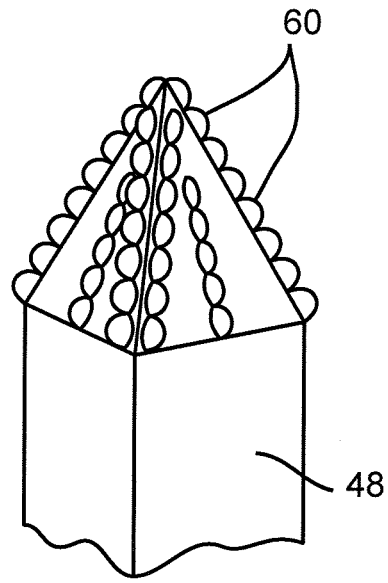
FIG. 13 illustrates another embodiment of the invention where the nanoscopic structures 60 are in the form of plumes of amorphous material supported on the microscopic columnar structure 48.

FIG. 13 illustrates another embodiment of the invention where the nanoscopic structures 60 are in the form of plumes of amorphous material supported on the microscopic columnar structures 48, such as of titanium nitride.

Figure 14:
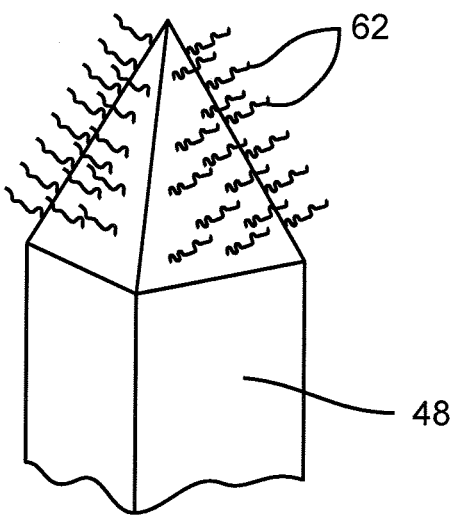
FIG. 14 illustrates still another embodiment of the invention where the nanoscopic structures 62 are in the form of filaments supported on the microscopic columnar structure 48.

FIG. 14 illustrates still another embodiment of the invention where the nanoscopic structures 62 are in the form of filaments supported on the microscopic columnar structures 48, such as of titanium nitride.

In any event, the result is an implantable electrode having the requisite biocompatibility and biostability characteristics, such as provided by columnar titanium nitride, but with improved high specific surface area characteristics. The electrode also exhibits a relatively lower polarization rise upon a stimulation event than is currently provided by microscopic columnar titanium nitride, and the like, devoid of the added nanoscopic structures.

Figure 15:
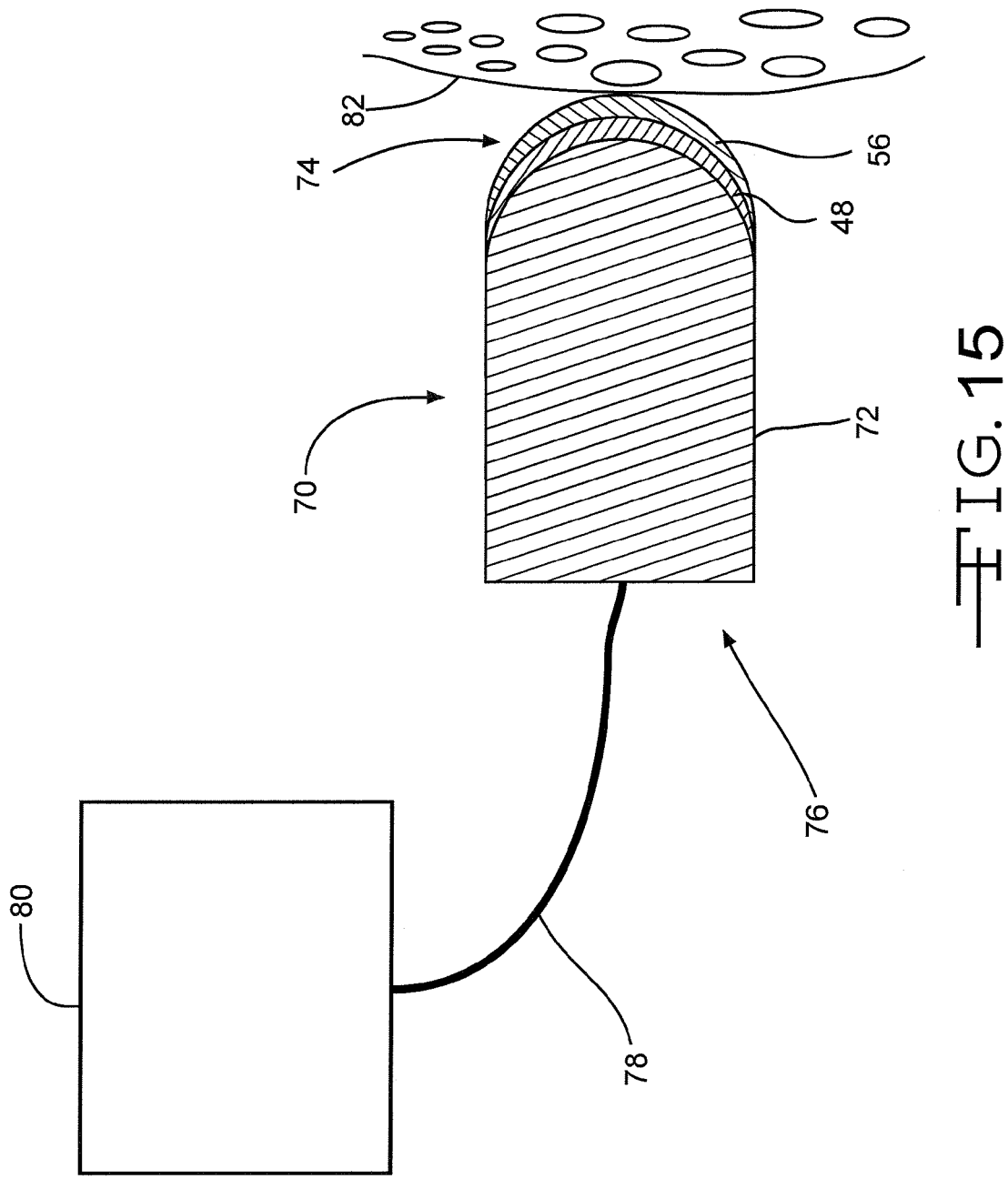
FIG. 15 is a cross-sectional side view of an electrode 70 connected to a pulse generator 80 by an electrical conductor 78 according to the present invention.

FIG. 15 shows an electrode 70 according to the present invention. The electrode 70 has a substrate 72 with a first end 74 and a second end 76. The substrate 72 is preferably of 90% platinum/10% iridium among others that have previously been discussed. The first end 74 has a coating supported on the substrate 72 according to the present invention in which nanoscopic surface structures 56 have been deposited on the exposed surface of the microscopic columnar structures 48. The respective structures 48, 56 are shown as layers, but that is for the purpose of illustration only. A more accurate depiction is as shown in FIG. 11. The microscopic columnar structures 48/nanoscopic structures 56 are an outer surface of the electrode 70.

In use, the second end 76 of the electrode 70 receives electricity to be delivered to the first end 74. The second end 76 may be electrically connected via an electrical conductor 78 to an electrical pulse generator 80, for example a cardiac pacemaker. When connected to a cardiac pacemaker 80, the first end 74 senses signals from the heart tissue 82 and delivers them to the cardiac pacemaker 80 via the electrical conductor 78. The pulse generator 80 then sends electrical pulses down the conductor 78 to the electrode 70 and into the heart 82 to provide the needed therapy in an improved low energy loss or low impedance transmission. The electrode 70 including the nanoscopic surface structures 56 deposited on the exposed surface of the microscopic columnar structures 48 and the electrical conductor 78 form a lead assembly.

The following examples describe the manner and process of providing a coated electrode according to the present invention, and they set forth the best mode contemplated by the inventors of carrying out the invention, but they are not to be construed as limiting.

EXAMPLE I

A number of machined electrodes comprising platinum/20% iridium provided with a sintered platinum/10% iridium coating were sputter coated with columnar titanium nitride (TiN) according to the protocol in Table 1. Power "A" is with the cathode positioned parallel to the sample holder. Power "B" is with the cathode mounted at a 40 degree angle to the sample holder.

TABLE 1

| Step # | Time (incremental, min) | Power A (W) | Power B (W) | Pressure (Torr) | Air flow (sccm) | N flow (sccm) |
|---|---|---|---|---|---|---|
| 1 | 10 | 3000 | 3000 | $8^{-3}$ | 75 | 0 |
| 2 | 10 | 3000 | 3000 | $8^{-3}$ | 0 | 100 |
| 3 | 285 | 3000 | 3000 | $8^{-3}$ | 75 | 75 |

The sputter deposited titanium nitride had a high specific surface area due to its columnar structure with crystallite microscopic diameters of about 100 nm to about 500 nm.

Figure 16:
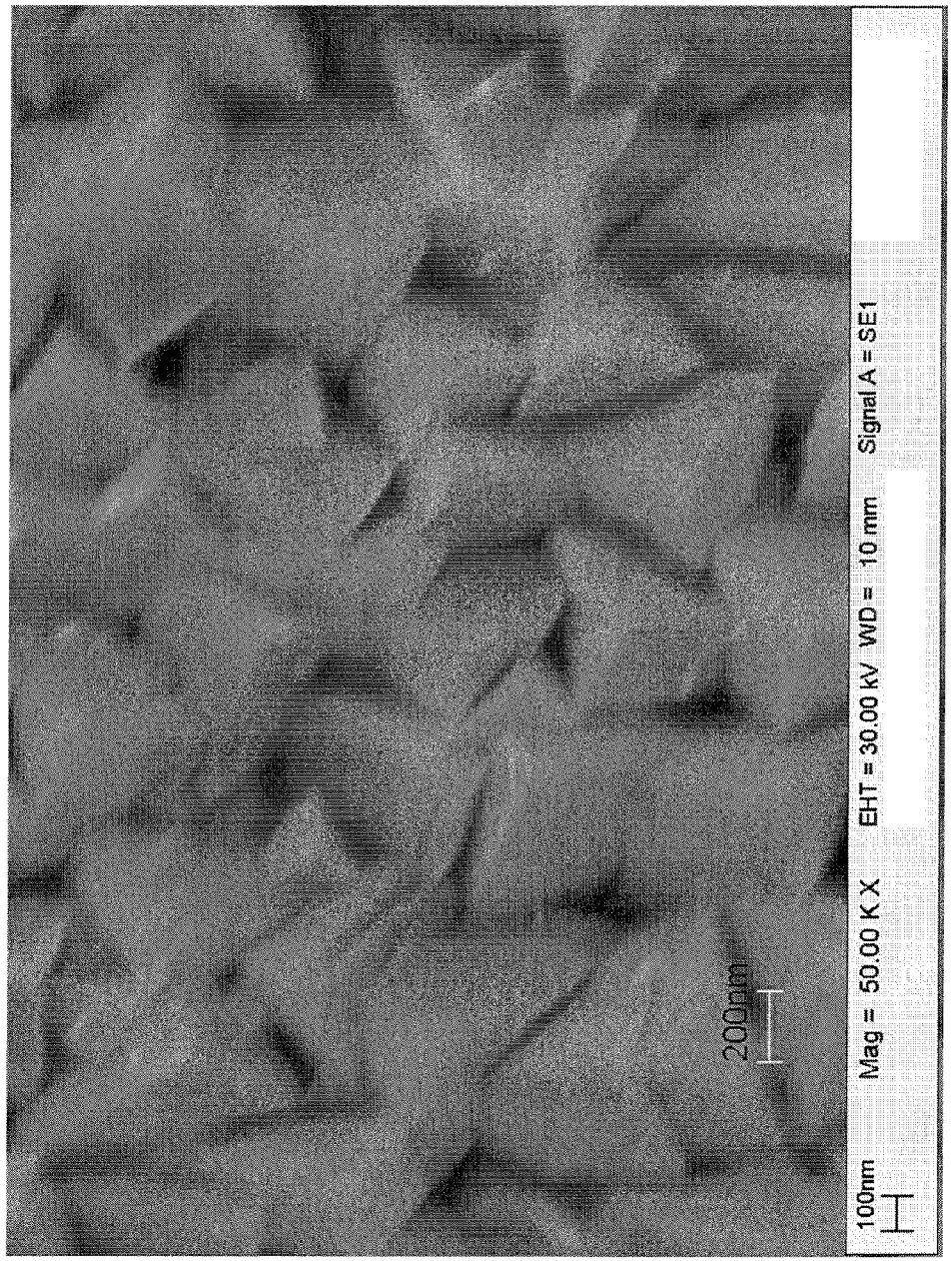
FIGS. 16 and 17 are photographs showing representative single morphology pictures of uniform 200 nm to 500 nm structures at 50,000× and 90,000×, respectively, according to conventional practice.
Figure 17:

FIGS. 16 and 17 show representative single morphology pictures of uniform 200 nm to 500 nm structures at 50,000× and 90,000×, respectively.

EXAMPLE II

Then, nanoscopic TiN was deposited on the exposed surfaces of the microscopic structures formed in Example I using the protocol shown in Table 2. Power "A" was with the cathode mounted parallel to the sample holder. Power "B" was with the cathode mounted at a 40 degree angle to the sample holder.

TABLE 2

| Step # | Time (incremental, min) | Power A (W) | Power B (W) | Pressure (Torr) | Air flow (sccm) | N flow (sccm) |
|---|---|---|---|---|---|---|
| 1 | 10 | 3000 | 3000 | $8^{-3}$ | 75 | 0 |
| 2 | 10 | 3000 | 3000 | $8^{-3}$ | 0 | 100 |
| 3 | 285 | 3000 | 3000 | $8^{-3}$ | 75 | 75 |
| 4 | 100 | 2500 | 3000 | $22^{-3}$ | 75 | 75 |

Figure 18:
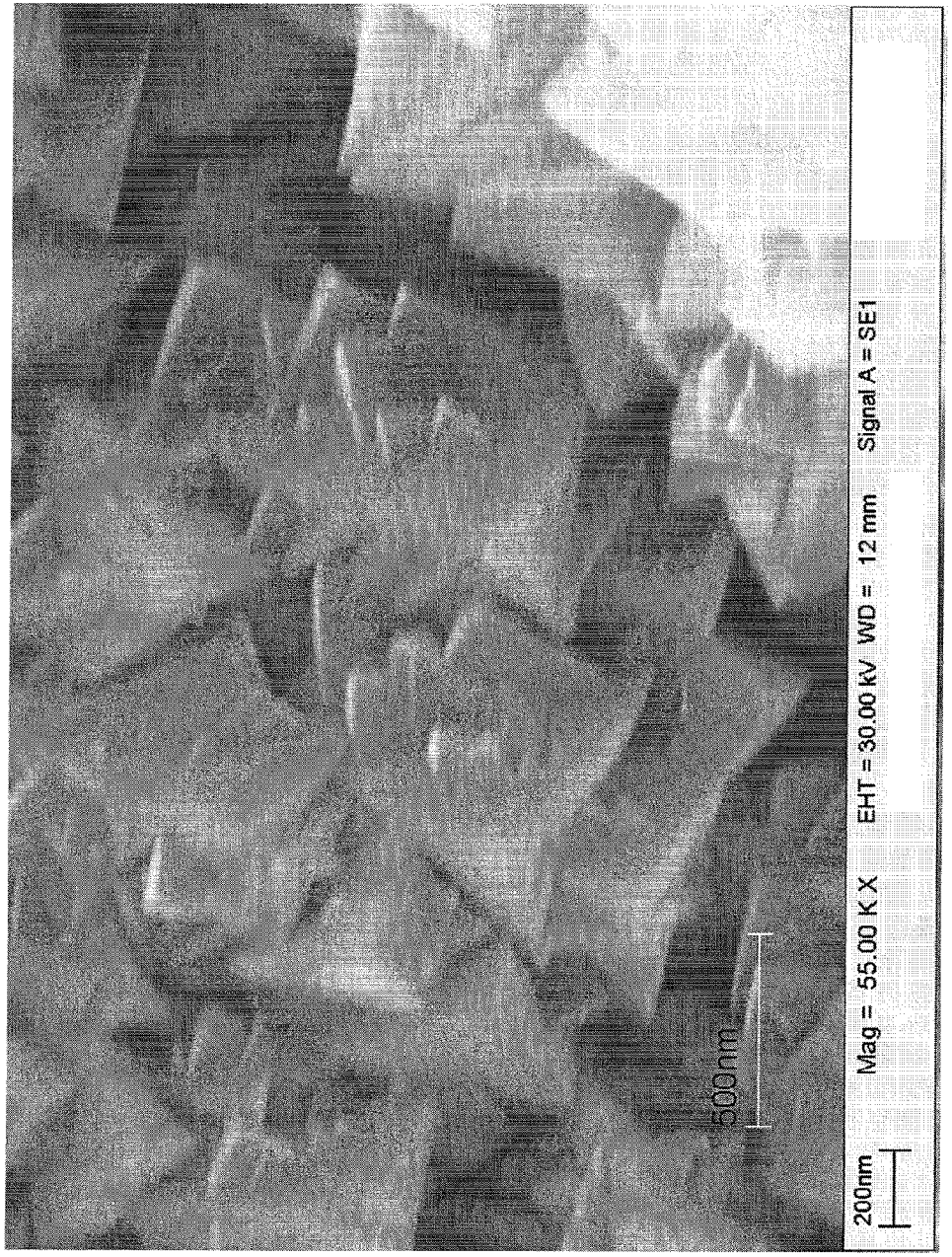
FIGS. 18 and 19 are photographs showing the present invention "dual morphology" coating having nanoscopic structures supported on the microscopic columnar structures shown in FIGS. 16 and 17 at 55,000× and 30,000×, respectively.
Figure 19:
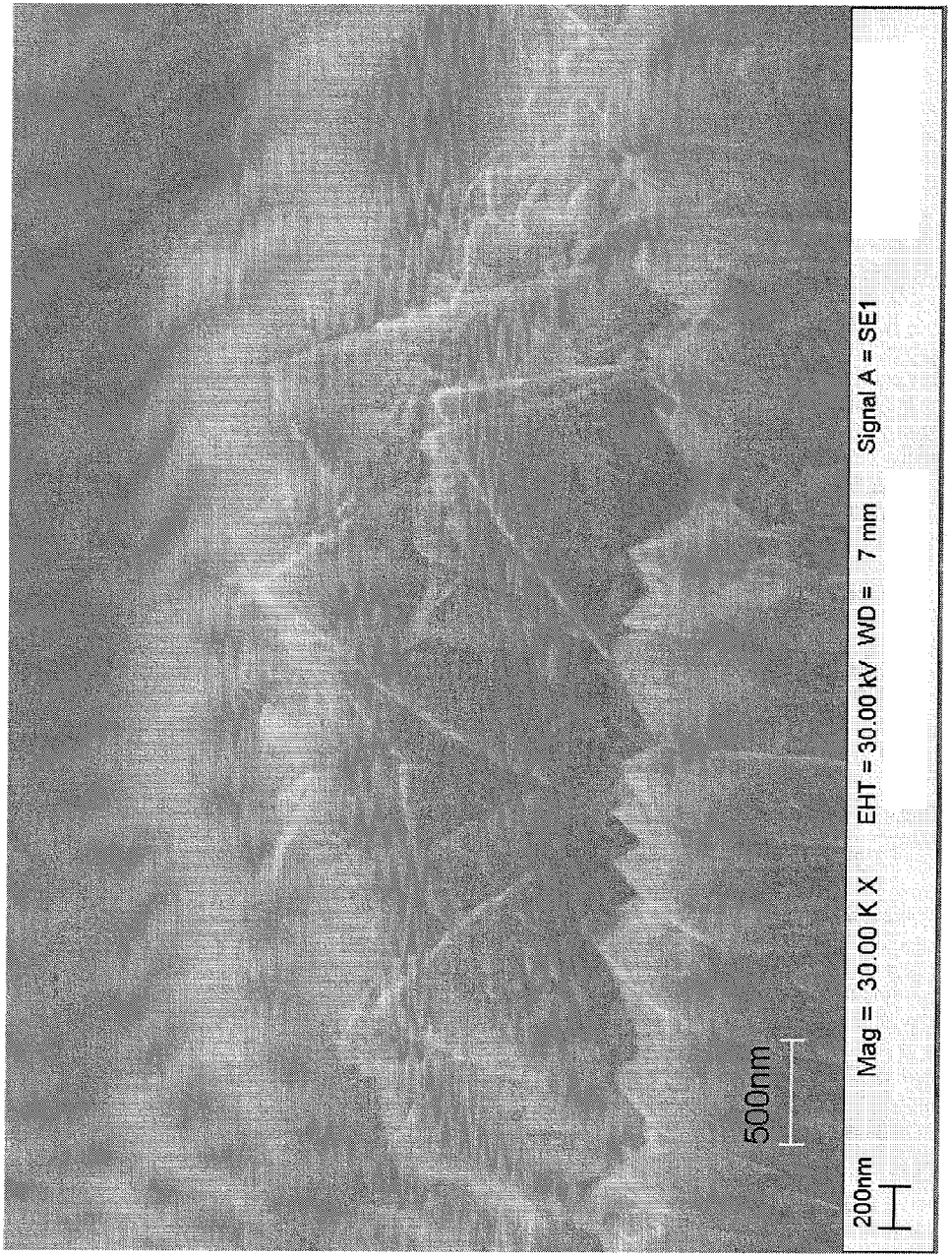

FIGS. 18 and 19 show an example of the present invention "dual morphology" coating having the nanoscopic structures supported or "grown on top of" the microscopic columnar structures at 55,000× and 30,000×, respectively. Note that the secondary nanoscopic structures are supported on the primary microscopic structures of the conventional electrode. These secondary features were deposited under a relatively high pressure of greater than about 20 mTorr. Both features were made without removing the substrates from vacuum.

It is known that the capacitance of a coated electrode can be used as a measure of its specific surface area based on the creation of a capacitance double layer. This layer is often measured using electrical impedance spectroscopy (EIS) in which a sine waveform with a small potential is applied around the open circuit potential of the system. The resulting data is then used to determine the capacitance of the system using well-developed methods and models.

FIG. 20 is a graph showing the EIS results of an electrode made according to Example I, curve 90, in comparison to the same electrode after having undergone further processing according to Example II, curve 92. The relatively lower impedance of the present coating reflects a two fold increase in capacitance at 100 mHz as compared to that of the conventional electrode.

Although TiN is a preferred material for both the macroscopic and nanoscopic features of the electrode, the technique of decreasing feature size by decreasing mobility and therefore increasing nucleation sites is applicable for most known materials. It is therefore important to choose a material that is biocompatible and stable under anodic and cathodic conditions. While TiN has been used for the purpose of demonstration, it is understood that any material which satisfies the requirements of being both biostable and biocompatible can be used. Suitable materials include carbon, boron, platinum, palladium, iridium, gold, titanium, tantalum, niobium, ruthenium, zirconium, and alloys thereof. In addition, carbides, nitrides, carbonitrides, and oxides or doped oxides of these metals and their alloys can be used.

While this invention has been described in conjunction with preferred embodiments thereof, it is evident that many alternatives, modifications, and variations will be apparent to those skilled in the art. Accordingly, it is intended to embrace all such alternatives, modifications and variations that fall within the broad scope of the appended claims.

What is claimed is:

1. An implantable electrode, comprising:
   a) a substrate selected from the group consisting of tantalum, titanium, zirconium, iridium, platinum, palladium, niobium, and mixtures thereof;
   b) microscopic surface structures directly contacting at least a portion of the substrate, wherein the microscopic surface structures are of a first material in the form of columnar structures providing inter-columnar porosity between adjacent columns, and wherein the first material is selected from the group consisting of a nitride of the group consisting of boron, platinum, palladium, iridium, gold, titanium, tantalum, niobium, ruthenium, zirconium, and alloys and mixtures thereof; and
   c) secondary nanoscopic surface structures supported directly on the microscopic surface structures, wherein the secondary nanoscopic surface structures comprise a second material selected from the group consisting of a carbide, a nitride, a carbonitrides, and an oxide of the group consisting of carbon, boron, platinum, palladium, iridium, gold, titanium, tantalum, niobium, ruthenium, zirconium, and alloys and mixtures thereof.

2. The implantable electrode of claim 1 wherein the microscopic surface structures range from about 100 nm to about 1000 nm, 3. The implantable electrode of claim 1 wherein the nanoscopic surface structures have features of less than about 50 nm.

4. The implantable electrode of claim 1 wherein the first material of the microscopic surface structures and the second material of the nanoscopic surface structures are of the same material.

5. The implantable electrode of claim 1 wherein the first material of the microscopic surface structures and the second material of the nanoscopic surface structures are of different materials.

6. The implantable of claim 1 wherein the first material of the microscopic surface structures and the second material of the nanoscopic surface structures are selected from the group consisting of iridium nitride, titanium nitride, tantalum nitride, niobium nitride, ruthenium nitride, zirconium nitride, and mixtures thereof.

7. The implantable electrode of claim 1 wherein the microscopic surface structures provide both inter-columnar and intra-columnar porosity.

8. The implantable electrode of claim 1 being configured for delivery of an electrical pulse to body tissue.

9. A cardiac pacing lead assembly, comprising:
   a) an implantable electrode, comprising:
      i) a substrate selected from the group consisting of tantalum, titanium, zirconium, iridium, platinum, palladium, niobium, and mixtures thereof;
      ii) microscopic surface structures directly contacting at least a portion of the substrate and configured for transmission of an electrical pulse to tissue, wherein the microscopic surface structures are of a first material in the form of columnar structures providing inter-columnar porosity between adjacent columns; and
      iii) secondary nanoscopic surface structures of a second material supported directly on the microscopic surface structures,
      iv) wherein the first material of the microscopic surface structures and the second material of the nanoscopic surface structures are selected from the group consisting of a nitride of the group consisting of boron, platinum, palladium, iridium, gold, titanium, tantalum, niobium, ruthenium, zirconium, and alloys and mixtures thereof; and b) an electrical conductor electrically connected to the implantable electrode.

10. The cardiac pacing lead assembly of claim 9 wherein the microscopic surface structures range from about 100 nm to about 1000 nm.

11. The cardiac pacing lead assembly of claim 9 wherein the nanoscopic surface structures have features of less than about 50 nm.

12. The cardiac pacing lead assembly of claim 9 wherein the first material of the microscopic surface structures and the second material of the nanoscopic surface structures are selected from the group consisting of iridium nitride, titanium. nitride, tantalum nitride, niobium nitride, ruthenium nitride, zirconium nitride, and mixtures thereof.

13. The cardiac pacing lead assembly of claim. 9 wherein the substrate is of platinum/10% iridium.

14. The cardiac pacing lead assembly of claim 9 wherein the microscopic surface structures provide both inter-columnar and intra-columnar porosity.

15. The cardiac pacing lead assembly of claim 9 wherein the first material of the microscopic surface structures and second material of the nanoscopic surface structures are of the same material.

16. The cardiac pacing lead assembly of claim 9 wherein the first material of the microscopic surface structures and the second material of the nanoscopic surface structures are of different materials.

17. The cardiac pacing lead assembly of claim 9 being configured for delivery of an electrical pulse to body tissue.

18. An implantable electrode, comprising:
a) a substrate selected from the group consisting of tantalum, titanium, zirconium, iridium, platinum, palladium, niobium, and mixtures thereof;
b) microscopic surface structures directly contacting at least a portion of the substrate, wherein the microscopic surface structures comprise columnar titanium nitride; and
c) secondary nanoscopic surface structures supported directly on the titanium nitride microscopic surface structures, wherein the nanoscopic surface structures comprise titanium nitride.

19. The implantable electrode of claim 18 wherein the macroscopic and nanoscopic surface structures consist essentially of titanium nitride having both inter-columnar and intra-columnar porosity.

20. A method for making an implantable electrode, comprising the steps of:
a) selecting a substrate from the group consisting of tantalum, titanium, zirconium, iridium, platinum, palladium, niobium, and mixtures thereof;
b) depositing microscopic surface structures in the form of columnar structures providing inter-columnar porosity between adjacent to columns directly onto the substrate, the microscopic surface structures being of a first material selected from the group consisting of a nitride of the group consisting of boron, platinum, palladium, iridium, gold, titanium, tantalum, niobium, ruthenium, zirconium, and alloys and mixtures thereof; and
c) depositing nanoscopic surface structures directly onto the microscopic surface structures, the nanoscopic surface structures being of a second material selected from the group consisting of a carbide, a nitride, a carbonitrides, and an oxide of the group consisting of carbon, boron, platinum, palladium, iridium, gold, titanium, tantalum, niobium, ruthenium, zirconium, and alloys and mixtures thereof.

21. The method of claim 20 including providing the first material of the microscopic surface structures and the second material of the nanoscopic surface structures being of the same material.

22. The method of claim 20 including providing the first material of the microscopic surface structures and the second material of the nanoscopic surface structures being of different materials.

23. The method of claim 20 including providing the microscopic surface structures ranging from about 100 nm to about 1000 nm and providing the nanoscopic surface structures being less than about 50 nm.

24. The method of claim 20 including selecting the first material of the microscopic surface structures and the second material of the nanoscopic surface structures from the group consisting of iridium nitride, titanium nitride, tantalum nitride, niobium nitride, ruthenium nitride, zirconium nitride, and mixtures thereof.

25. The method of claim 20 including providing the substrate being of platinum/10% iridium.

26. The method of claim 20 including providing the microscopic surface structures having both inter-columnar and intra-columnar porosity.

* * * * *